United States Patent [19]

Horrobin et al.

[11] 4,328,243

[45] May 4, 1982

[54] MANIC-DEPRESSIVE ILLNESSES

[76] Inventors: David F. Horrobin, P.O. Box 10, Nuns' Island, Montreal, Canada, H3E 1J8; Julian Lieb, 41 Village La., Bethany, Conn. 06525

[21] Appl. No.: 251,901

[22] Filed: Apr. 7, 1981

[51] Int. Cl.³ .................. A61U 31/20; A61U 31/265
[52] U.S. Cl. .................................... 424/301; 424/318
[58] Field of Search ............................... 424/318, 301

*Primary Examiner*—Stanley J. Friedman
*Attorney, Agent, or Firm*—Schwartz, Jeffery, Schwaab, Mack, Blumenthal & Koch

[57] ABSTRACT

A method for the treatment and/or prophylaxis of the side-effects of lithium treatment in a subject suffering from manic-depressive psychosis, which method comprises administering to the subject an effective amount therefor of dihomogamma-linolenic acid and/or a biosynthetic precursor thereof.

3 Claims, No Drawings

MANIC-DEPRESSIVE ILLNESSES

This invention relates to the treatment of manic-depressive illnesses.

The administration of lithium, and in particular lithium salts such as lithium carbonate, has found widespread application in the treatment of manic-depressive psychosis. Lithium treatment has been reported as being particularly effective in the treatment of the manic phase of this illness and also in the prophylaxis of both manic and depressive relapses.

However, lithium treatment is often accompanied by a number of side-effects which are generally related to the dosage and degree of accumulation. In particular, side-effects which may occur include transient nausea, fine tremor, fatigue, muscular weakness, polydipsia and polyuria. In most patients these mild side-effects disappear after a week or so of continued treatment, but thirst, excessive urination and tremor often persist. In a significant proportion of patients, however, more serious side-effects may occur and these include ataxia, coarse tremor, confusion, diarrhoea, drowsiness, fasciculation and slurred speech. When such serious side-effects occur it is necessary to withdraw treatment from the patient.

Prostaglandin E1 (PGE1) is a compound which has been found to be of importance in the maintenance of the normal body metabolism, and this compound is synthesised in the body from its bioprecursor, dihomo-gamma-linolenic acid (DGLA). In order, therefore, to ensure that physiologically acceptable amounts of PGE1 are maintained in the body, it is necessary to provide sufficient DGLA and make sure that the conversion of DGLA to PGE1 proceeds normally. DGLA is itself biosynthesised from the precursor substance, gamma-linolenic acid, and in turn this latter substance is biosynthesised from linoleic acid.

We have found that lithium can inhibit or block the conversion of DGLA stored in the body to PGE1, and it is believed that this may, at least in part, be responsible for any side-effects exhibited in lithium treatment.

It is an object of the present invention to alleviate the side-effects of the treatment of a subject suffering from manic-depressive psychosis by administration of lithium salts.

Thus, in one aspect the present invention provides a method for the treatment and/or prophylaxis of the side-effects of lithium treatment in a subject suffering from manic-depressive psychosis, which method comprises administering to the subject an effective amount therefor of dihomogammalinolenic acid or a biosynthetic precursor thereof.

In another aspect, the invention provides a method for the treatment and/or prophylaxis of a manic-depressive psychosis in a subject which method comprises administering to the subject an effective amount therefor of a physiologically acceptable lithium salt conjointly with dihomogamma-linolenic acid or a biosynthetic precursor thereof in an amount effective to prevent the formation of the side-effects of lithium.

As indicated above dihomogamma-linolenic acid (DGLA) is a precursor for prostaglandin E1 (PGE1), and the administration of this substance conjointly with lithium treatment mitigates against the adverse effects on the conversion of DGLA to PGE1 in the body.

In the methods of treatment according to the invention, the DGLA may be replaced by an equivalent amount of a biosynthetic precursor thereof such as the above-mentioned gamma-linolenic acid or linoleic acid. If desired, these substances may be administered in admixture. These substances may also be administered in the form of physiologically acceptable functional derivatives thereof such as, for example, their $C_1$–$C_4$ alkyl (e.g. methyl and ethyl) esters and the triglycerides of the acids. Convenient sources of linoleic acid for administration in the methods according to the invention are the many vegetable oils of which it forms a major constituent. Examples of such oils include cottonseed, soyabean, peanut, corn, sunflower seed, safflower, poppy seed, linseed and perilla oils, where the linoleic acid occurs in the form of its triglyceride. In the methods of the invention, these vegetable oils may be administered as such i.e. without any treatment to isolate the linoleic acid therefrom. When such oils are used in the methods of the invention, they may conveniently be administered in an amount of from 0.5 to 100 g per day in suitably divided doses.

At the present time known sources of oils having a high gamma-linolenic acid content are few. One source currently available is the seed of the Evening Primrose or *Oenothera biennis L*, the oil extract therefrom containing gamma-linolenic acid and linoleic acid in the form of their triglycerides. Another source of gamma-linolenic acid is the seed of *Borago officinalis* which provides a richer source of gamma-linolenic acid with smaller amounts of linoleic acid. Again, these seed oil extracts may be used as such or may, if desired, be fractionated to yield an oil composition enriched in the desired gamma-linolenic and/or linoleic acids.

Dihomogamma-linolenic acid for administration according to the invention may be prepared from gamma-linolenic acid according to known methods.

Convenient daily doses of dihomogamma-linolenic acid or gamma-linolenic acid in the methods according to the invention are, for example, from 50 mg to 100 g per day, suitably in divided doses.

Lithium treatment for manic-depressive psychosis is conveniently effected by administration of lithium carbonate, although other physiologically acceptable lithium salts may be employed. Lithium carbonate is generally administered orally in an initial dose of 250 or 300 mg daily, which may be gradually increased to 750 mg daily in divided doses. In severely affected subjects up to 2.0 g per day may be administered. The lithium plasma level is generally monitored, e.g. once or twice weekly, during the course of treatment and the rate of administration adjusted to produce a concentration of 0.5 to 1.6 mM. per liter in the plasma. As soon as an improvement in the psychological state of the subject is noted, the dosage is generally decreased and the maintenance level adjusted on the basis of the behaviour of the patient.

The invention will now be illustrated with reference to the following case histories, in which the results of clinical studies are presented.

CASE HISTORY 1

The patient was a 70 year old woman with a 20 year history of recurrent depressions. An initial good response to tranylcypromine could not be maintained despite high doses of the drug. On lithium carbonate, 300 mg/day, she developed tremors, confusion and diarrhoea and the lithium treatment was withdrawn. A second trial of lithium at 150 mg/day induced the same symptoms and again had to be stopped.

She was subsequently placed on safflower oil, 1500 mg twice per day, and lithium therapy was reinstituted. Lithium at 600 mg/day (serum level 0.7–0.8 mM/l) was tolerated for eight weeks without evidence of neurotoxicity. Her mood and level of functioning improved markedly.

CASE HISTORY 2

The patient was a 59 year old woman with a 15 year history of episodic excessive drinking. Within the week after ingesting one half to one pint of vodka in an evening's bout of drinking she would become tense and experience an irresistible craving for alcohol. This would culminate in the next bout of drinking.

Since lithium has been used in alcoholics, she took lithium carbonate, 600 mg/day, (serum level 0.5 mM/l) for five days but stopped it because of tremors, weakness and ataxia. When seen two days after stopping lithium she had tremor in both hands, intention tremor and ataxia. Within ten minutes of taking 2500 mg safflower oil, there was a marked reduction in the amplitude and frequency of the tremor, amelioration of the intention tremor and no evidence of ataxia. She reported considerable subjective relief. Twenty minutes after the linoleic acid administration there was no trace of tremor and it did not return.

CASE HISTORY 3

The patient was a 24 year old man with a four month history of agitated delusional depression. The delusions and agitation subsided on 1800 mg lithium carbonate/day (serum level 1.1 mM/l) but he developed hand tremors, intention tremor and ataxia. There was a marked reduction in the tremors and ataxia within 15 minutes of taking 2000 mg safflower oil. He has been free of tremors for one month on a daily regime of 1500 mg lithium carbonate and 5000 mg safflower oil.

CASE HISTORY 4

The patient was a 38 year old woman with a 20 year history of irritability, hyperactivity and left hemicranial migraines with an attack frequently of two or three headaches per week. Lithium carbonate (1500 mg/day, serum level 0.9–1.1 mM/l), removed the irritability and hyperactivity and reduced the migraine frequency to one per week. However she developed ataxia, dry skin, thirst, fluid retention, and tremors. Isocarboxazide (Marplan) 30 mg/day was substituted for lithium and she had four weeks free of headache. Unfortunately the irritability and hyperactivity returned and she complained of an inability to achieve sexual climax. Although she remained capable of sexual arousal, each stage was slow and of reduced intensity and she felt uncomfortable and restless after intercourse. At her request isocarboxazid was tapered off and discontinued. Two days after taking the last dose of isocarboxazid she developed an excruciating headache which was similar to a spinal tap headache she had experienced previously. She also developed sharp, stabbing pains in her fingers, toes, wrists, hands and feet. Safflower oil was then introduced into her treatment (1500 mg twice daily) and the headache and joint pains gradually subsided and disappeared. Lithium carbonate, 900 mg/day was then reintroduced because of increasing hyperactivity and irritability. After five days on the combined lithium/safflower oil regime she felt relaxed and free of irritability. However tremor and ataxia then returned and she became unable to write legibly. The dose of safflower oil was increased to 2500 mg twice a day and the tremor and ataxia disappeared.

CASE HISTORY 5

The patient was a 71 year old man with a 25 year history of bipolar manic depressive illness. His mood swings were controlled by lithium carbonate (1350 mg/day, serum level 0.7–0.8 mM/l), with tranylcypromine, 20 mg/day, as an adjunct for depressive episodes.

In his 71st year he became increasingly intolerant of lithium. His vision became blurred and he developed peripheral edema, tremor, weakness and ataxia. The lithium dose was lowered to 600 mg/day but his weakness progressed so that he could not walk. Lithium was discontinued and the toxic symptoms disappeared, but florid manic symptomatology supervened so that lithium had to be reintroduced. At a dose of only 300 mg lithium carbonate per day, toxic symptoms reappeared and he was again unable to walk.

Within 20 minutes of taking 2000 mg of safflower oil he reported markedly improved muscle control, coordination and strength. There was no tremor and only slight ataxia. The mania remitted on a daily regimen of 600 mg lithium carbonate and there was no re-emergence of toxic symptoms on a regimen of 400 mg safflower oil per day.

We claim:

1. Method for the treatment of the side-effects of lithium treatment in a subject suffering from manic-depressive psychosis and undergoing lithium treatment, which method comprises orally administering to said subject an effective amount of dihomogamma-linolenic acid and/or gamma-linolenic acid or linoleic acid.

2. A method according to claim 1, wherein there is conjoint administration acceptable lithium salt with the acid.

3. A method according to claim 2 wherein the lithium salt is lithium carbonate.

* * * * *